US009527010B2

(12) United States Patent
Williams et al.

(10) Patent No.: US 9,527,010 B2
(45) Date of Patent: Dec. 27, 2016

(54) SEPARATION SYSTEM AND METHOD

(75) Inventors: Alan M. Williams, Easton, PA (US);
Adam Kaletski, Hillsborough, NJ (US);
Lisa Stack, Westfield, NJ (US); Daniel Go, Parsippany, NJ (US); John Krasnansky, Hillsborough, NJ (US);
David A. Wareheim, Audubon, PA (US); Bin Lin, Phoenixville, PA (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 615 days.

(21) Appl. No.: 12/566,701

(22) Filed: Sep. 25, 2009

(65) Prior Publication Data

US 2011/0073548 A1 Mar. 31, 2011

(51) Int. Cl.

| | |
|---|---|
| *B01D 35/14* | (2006.01) |
| *C02F 1/00* | (2006.01) |
| *C12M 1/00* | (2006.01) |
| *B01D 15/18* | (2006.01) |
| *G01N 30/28* | (2006.01) |
| *G01N 30/46* | (2006.01) |
| *G01N 30/24* | (2006.01) |

(Continued)

(52) U.S. Cl.
CPC ........... *B01D 15/1871* (2013.01); *G01N 30/28* (2013.01); *G01N 30/465* (2013.01); *B01D 15/1864* (2013.01); *B01D 15/362* (2013.01); *G01N 30/24* (2013.01); *G01N 30/34* (2013.01)

(58) Field of Classification Search
USPC ....... 210/134, 739, 102; 435/283.1; 530/412
See application file for complete search history.

(56) References Cited

U.S. PATENT DOCUMENTS 3,918,907 A * 11/1975 Stephens .................. 436/89
4,246,101 A * 1/1981 Selby, III ............ B01J 49/0021
210/143

(Continued)

FOREIGN PATENT DOCUMENTS

| EP | 1 544 611 | 6/2005 |
|---|---|---|
| JP | 62-255865 | 11/1987 |

(Continued)

OTHER PUBLICATIONS

JP Notice of Preliminary Rejection Dated Feb. 18, 2014 Issued on Corresponding JP Application No. 2012-530844.

(Continued)

*Primary Examiner* — Joseph Drodge
*Assistant Examiner* — Richard Gurtowski
(74) *Attorney, Agent, or Firm* — Wood IP LLC (57) ABSTRACT

A separation system comprises (i) at least two separation units, each separation unit comprising a fluid inlet and a fluid outlet, wherein the separation units are connected in series outlet to inlet to form a line of separation units, and (ii) sensing and adjustment means, provided in-line between each separation unit, for continuously monitoring and adjusting at least one environmental property parameter of fluid flowing from one separation unit to a subsequent separation unit in the line of separation units. Uses of the separation system and a method for purification of a liquid containing a desired species, using separation units and in-line adjustment of a fluid flow or flows, are also disclosed.

20 Claims, 4 Drawing Sheets

(51) Int. Cl.
*G01N 30/34* (2006.01)
*B01D 15/36* (2006.01)

(56) References Cited

U.S. PATENT DOCUMENTS

| | | | |
|---|---|---|---|
| 4,840,730 A * | 6/1989 | Saxena | B01D 15/1807 210/103 |
| 5,114,576 A * | 5/1992 | Ditzler et al. | 210/195.1 |
| 5,234,586 A * | 8/1993 | Afeyan | G01N 27/44717 204/603 |
| 2003/0170810 A1 * | 9/2003 | Vedadi et al. | 435/69.1 |
| 2004/0061069 A1 * | 4/2004 | Schalble et al. | 250/432 R |
| 2004/0124253 A1 * | 7/2004 | Bergwin | B05B 12/10 239/10 |
| 2005/0139530 A1 * | 6/2005 | Heiss | 210/85 |
| 2007/0039375 A1 | 2/2007 | Chaintreau et al. | |
| 2008/0124245 A1 * | 5/2008 | Ito et al. | 422/82.05 |
| 2009/0050567 A1 | 2/2009 | Aumann et al. | |
| 2009/0126466 A1 | 5/2009 | Gilar et al. | |
| 2009/0149638 A1 | 6/2009 | Ley et al. | |

FOREIGN PATENT DOCUMENTS

| | | |
|---|---|---|
| JP | 01-096556 | 4/1989 |
| WO | WO 03/083467 | 10/2003 |
| WO | WO 2005-113457 | 12/2005 |
| WO | WO 2007-043874 | 4/2007 |
| WO | WO 2007/043874 | 4/2007 |
| WO | WO 2008-127087 | 10/2008 |
| WO | WO 2008/127087 | 10/2008 |
| WO | WO 2010/124159 | 10/2010 |

OTHER PUBLICATIONS

Decrop, W., et al., Chromatography Today, Jun. 2009, pp. 8-10.
Luellau, E., et al., Journal of Chromatography A, vol. 796, 1998, pp. 165-175.
Extended European Search Report Dated Jun. 2, 2014 Issued on Corresponding EP Application No. 10819116.4.
Decrop, W., et al., Chromatography Today, Jun. 2009, 8-10.
Luellau, E., et al., Journal of Chromatography A, 796 (1998) 165-175.

* cited by examiner

SEPARATION SYSTEM AND METHOD

FIELD OF THE INVENTION

The present invention relates to the separation and purification of compounds, especially biomolecules, and more particularly to a separation system performing multiple separation steps.

BACKGROUND OF THE INVENTION

During the past decade, there has been a tremendous growth in the use of proteins, such as monoclonal antibodies, for drug development and therapeutic applications. The production of pharmaceutical-grade monoclonal antibodies in large-scale, however, is a complex process requiring multiple chromatography and filtration steps to satisfy stringent regulatory requirements.

The manufacturing of biomolecules begins with the synthesis of the desired biological material in a biologically derived system. Preparation of the desired material is typically accomplished through a specifically designed and ordered series of physical separation techniques.

The manufacturing process for monoclonal antibodies, for example, typically includes expression in recombinant mammalian cell cultures. After centrifugation, the culture product is subjected to downstream purification (DSP) which generally comprises a "capture" stage, an "intermediate purification" stage and a "polishing" stage. The capture stage is usually based on Protein A affinity chromatography. The resulting product is then further purified and polished, typically using cation exchange and anion exchange chromatography steps to remove degradation products and impurities. Finally, viral species are removed through an included filtration step.

Protein A affinity chromatography, however, suffers from several disadvantages, including protein A leakage, and a simplified purification process has therefore been developed where a cation exchange capture stage replaces the protein A affinity chromatography. The cation capture step then removes process-related contaminants to such a low level that a single polishing step is enough to clean the residuals. Such a down stream purification of process monoclonal antibody thus includes a cation exchange chromatography step, an anion exchange chromatography step, and a virus removal filtration step.

The hitherto used down stream purification processes are performed with batch processes using hold-up tanks between the different chromatography and filtration steps. Each process step uses buffer or buffers of a certain pH and conductivity as well as post-process cleaning and storage liquids. Prior to each step, it is often necessary to adjust the conditions such as pH and protein concentration of the product stream, these adjustment steps then being performed as separate intermediate batch operations.

Separation systems and processes which to at least some extent allow for automation and on-line adjustment of eluates have been proposed in the prior art.

US 2009-0149638 discloses systems and processes for downstream protein purification on a large scale and which allow for automation, the processes being capable of being operated on a high-throughput and continuous basis. In the processes, one chromatography step follows another without an intermediate ultrafiltration/diafiltration step, the eluate from one tank being transferred to another via intermediate holding tanks which can be rendered acidic or basic.

US 2009-0126466 discloses multi-dimensional high performance liquid chromatography (HPLC) wherein a first chromatographic separation is performed at a first pH with a first mobile phase, and the fraction or fractions collected therefrom are subjected to a second chromatographic separation at a second different pH with a second mobile phase. The fraction or fractions collected from the first separation may be concentrated or diluted, optionally on-line, prior to subjecting the fraction or fractions to the second chromatographic separation mode.

It is an object of the present invention to provide an improved automated separation system which is capable of further reducing development time, processing time and cost of goods and which does not require intermediate holding tanks.

SUMMARY OF THE INVENTION

According to the present invention, the above and other objects and advantages are achieved by a separation or purification system comprising several separation units connected in series to form a single unit of operation and wherein means, preferably closed loop means, are provided in-line between each separation unit for measuring and adjusting measured parameters of the fluid flow between the separation units. Such a system will shorten the operation time and eliminate intermediate hold and intermediate testing requirements as are, for example, required for monoclonal antibody manufacturing.

The above inventive concept is, however, not restricted to downstream purification (DSP) or to separation units in the form of chromatography columns or filters and to the purification of proteins, such as antibodies. On the contrary, the invention is generally applicable to any separation or purification of chemical or biochemical species, downstream as well as upstream of its production.

In one aspect, the present invention therefore provides a separation system that includes at least two separation units. Each separation unit includes a fluid inlet and a fluid outlet, wherein the separation units are connected in series outlet to inlet to form a line of separation units. The separation system also includes a sensing and adjustment means that is provided in-line between each separation unit. The sensing and adjustment means is configured to continuously monitor and adjust at least one environmental property parameter of fluid flowing from one separation unit to a subsequent separation unit in the line of separation units.

This separation system comprises a plurality of separation units, each separation unit comprising a fluid inlet and a fluid outlet. The separation units are connected in series, outlet to inlet, to form a line of separation units. Between each separation unit, sensing and adjustment means are provided in-line for monitoring and adjusting at least one environmental property parameter of fluid flowing from one separation unit to a subsequent separation unit in the line of separation units.

The term "separation unit" as used herein is to be interpreted broadly and encompasses, for example, chromatographic devices, including columns and membranes, filters, centrifuges, two-phase separation devices, etc.

Also the term "environmental property parameter" as used herein and referring to fluid flowing in the system, is to be interpreted broadly and encompasses, for example, physical parameters of the fluid, such as conductivity, pressure, viscosity, temperature, refractive index, turbidity, flow rate; and chemical parameters, such as pH, concentration of species (e.g. product, salt), total organic carbon (TOC).

The separation system preferably comprises a computerized control and data analysis system for operation of the separation system.

In another aspect, the present invention includes a method for purifying a liquid containing at least one desired species. The method includes flowing the liquid to a first separation unit to a obtain a purified fluid outflow therefrom containing the desired species. The method also includes on-line monitoring and adjusting at least one environmental property parameter of the fluid outflow to a desired value. The method also includes directing the outflow to a second separation unit to obtain purified a fluid outflow therefrom containing the desired species and recovering the purified outflow containing the desired species.

This method for purifying a liquid containing at least one desired species, comprises the steps of (i) flowing the liquid to a first separation unit to a obtain a purified fluid outflow therefrom containing the desired species; (ii) on-line monitoring and adjusting at least one environmental property parameter of the fluid outflow to a desired value; (iii) directing the outflow to a second separation unit to obtain a purified fluid outflow therefrom containing the desired species; and (iv) recovering the purified outflow containing the desired species.

In a preferred embodiment, the method comprises subjecting the outflow from the second separation unit to at least one additional separation unit, wherein at least one environmental property parameter of the fluid inlet flow to each additional separation unit is monitored and adjusted to a desired value.

Preferably, method steps are controlled through a computerized control and data analysis system.

In still another aspect, the present invention comprises use of the separation system according to the first-mentioned aspect for studying biomolecules.

In yet another aspect, the present invention comprises use of the separation system according to the first-mentioned aspect for developing separation methodologies.

A more complete understanding of the present invention, as well as further features and advantages thereof, will be obtained by reference to the following detailed description and the accompanying drawings.

DETAILED DESCRIPTION OF THE INVENTION

As mentioned above, the present invention generally relates to a separation or purification system where multiple separation units are connected in series to form a single unit of operation, and which comprises in-line sensing and adjustment means between each separation unit. In the following, the invention will be described in more detail, by way of example only, with regard to a non-limiting embodiment thereof in the form of a downstream purification system for antibody, specifically monoclonal antibody.

The separation system, which may be referred to as a straight through processing (STP) system, integrates multiple chromatography steps and a viral filtration step in a single continuous process. A basic feature of the STP system is that it is designed to perform control of process parameters, including but not limited to pH, conductivity and UV absorbance of the product stream, preferably in a closed loop fashion.

Figure 1:
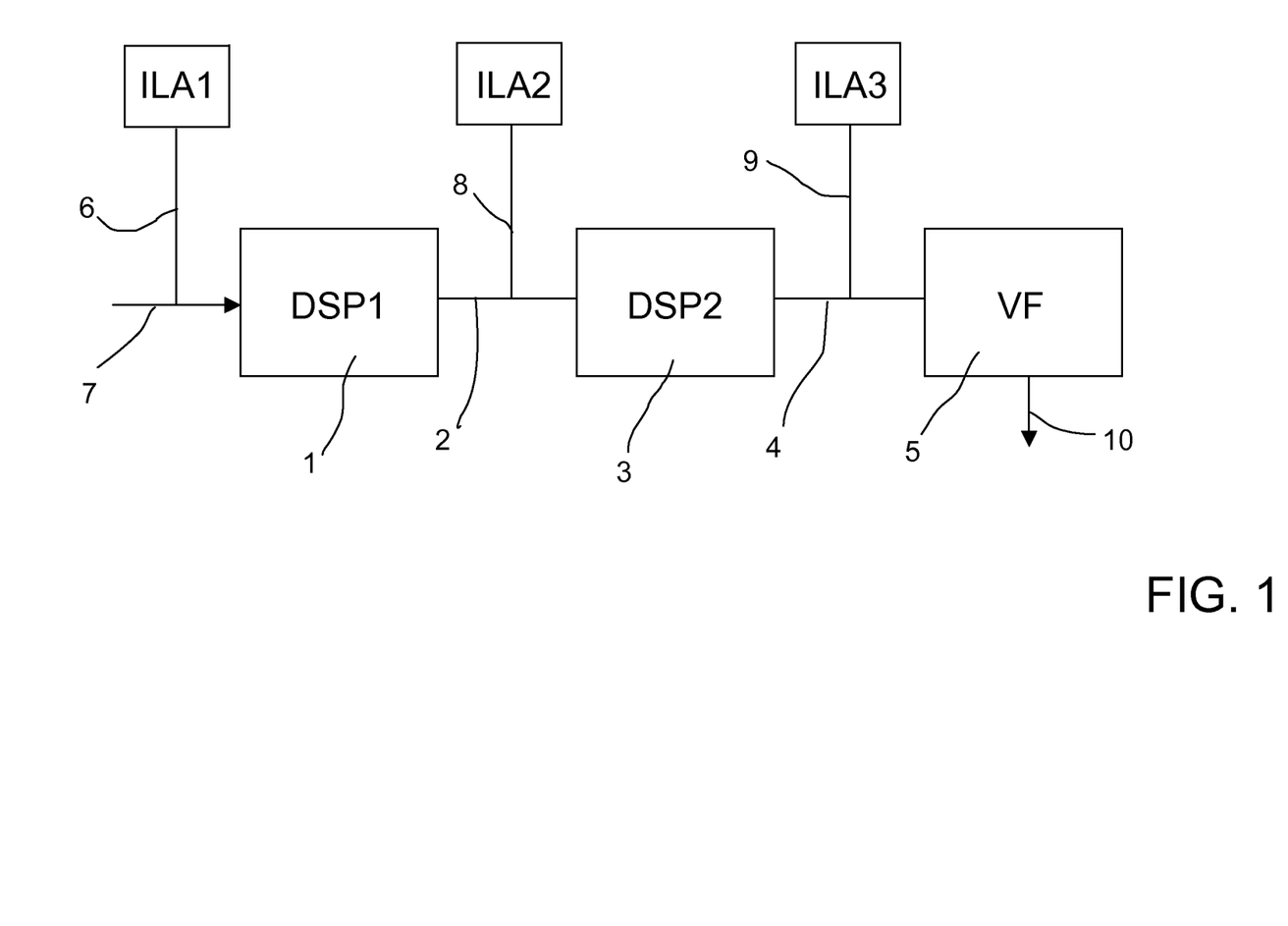
FIG. 1 is a diagrammatic illustration of a basic separation system configuration according to the present invention having three separation units.

FIG. 1 diagrammatically shows the basic configuration of an STP system according to the present invention, which here, for illustration and no limitation, has three separation units.

In FIG. 1, a first separation unit 1 (here called DSP1) is via its outlet connected by a direct conduit or pipe 2 to the inlet of a second separation unit 3 (here called DSP2). The outlet of the second separation unit 3 is then via a direct conduit 4 connected to the input of a third separation unit 5 (here called VF) so that the three separation units form a continuous line of separation units.

Between each separation unit 1, 3 and 5, there are provided means for in-line adjustment (ILA) for monitoring and control (up or down, i.e. boast or reduce). A first in-line adjustment means 6 is coupled to an inlet conduit 7 of the first separation unit 1, a second in-line adjustment means 8 is coupled to conduit 2 between the first and second separation units 1, 3, and a third in-line adjustment means 9 is coupled to conduit 4 between the second and third separation units 3, 5. It is understood that these in-line adjustment means replace the in-process sampling and process parameter tests for in conventional batch-based processing equipment. The in-line adjustments are made using sensors via closed loops (feed-back loops) resulting in the ability to respond instantly to anomalies as they occur, as will be described in more detail below.

A purified product-containing fluid flow is recovered from the virus removal filter 5 via an outlet conduit 10.

The different system units are typically mounted on a platform or skid. Further, the STP system is typically operated through a computerized control and data analysis system.

In case that the illustrated separation system would, for instance, be intended for downstream purification (DSP) of proteins, such as monoclonal antibodies, the three separation units would, for example, comprise two chromatographic columns and a virus removal filter in series, in FIG. 1 designated DSP1, DSP2 and VF, respectively. The first column DSP1 could then be a cation-exchange chromatography (CIEX) column, the second column DSP2 an anion-exchange chromatography (AIEX) column, and the virus removal filter VF, could, e.g., be a membrane filter. Alternatively, three different chromatographic columns could be used.

In such a case, the in-line environmental adjustments may, for example, include ionic strength (conductivity) adjustments to the product stream entering the first column (DSP1). Between the first (DSP1) and the second (DSP2) columns, in-line adjustment may include a change in pH and/or conductivity. Between the second column (DSP2) and the virus filtration (VF), in-line adjustment may include dilution (concentration of product), and optionally also pH. Buffers and other liquids used may be provided in tanks with previously prepared solution or be prepared in real time using an in-line preparation (in-line dilution) system, for example of the type described in co-pending application "Method and system for preparation of liquid mixtures", filed concomitantly herewith.

Compared to conventional batch-based downstream purification of monoclonal antibodies, the automated straight-through approach of the invention provides a streamlined process train with faster batch turnaround time, improved manufacturing facility utilization and throughput, elimination of vessels and additions to those vessels between steps, and lower processing costs. It also provides a more robust process through the sensor-based in-line adjustments.

The separation system of the invention will find wide application. Thus, in addition to direct product purification, also other applications will be greatly facilitated over existing manually intensive systems. Such applications include, for example, the study of biomolecules and the development of separation methodologies. Other applications include scale up and scale down studies for e.g. media and/or device life time, clearance studies, cleaning studies, just to mention a few.

The separation system will permit high accuracy to be obtained as well as high reproducibility.

It is understood that the separation system will provide control not only of the separation environment but also affect the environment of the molecules being separated. For instance, using low pH may inactivate viruses, pH, ionic strength and protein concentration may be brought to levels where the desired product is stable, proteases are inactive and/or unwanted aggregates can not form, etc.

As mentioned above, the in-line adjustments are made using sensors via closed loops (feed-back loops). A closed loop control system, in a simple design, comprises a process and a controller coupled in a closed loop. The process is influenced by its input signal (control signal). The measuring signal, i.e. the process output signal, provides information on the process to be controlled. The controller has two input signals, the measuring signal and set point which indicates the desired value of the measuring signal. The difference between these two signals initiates actions that will result in the actual response of the process to approach the desired response. This in turn drives the difference signal toward zero. More complicated control systems have multiple measuring signals and multiple control signals. Closed loop control systems are well known and need not be described in detail herein.

A commonly used closed loop controller is the PID (proportional-integral-derivative) controller. The PID controller calculates three separate parameters, i.e. the proportional, the integral and the derivative values. The proportional value determines the reaction to the current error, the integral value determines the reaction based on the sum of recent errors, and the derivative value determines the reaction based on the rate at which the error has been changing. The weighted sum of these three actions is used to adjust the portion of a control value.

In the in-line adjustment means outlined above, an in-line sensing device or sensor (detector) is coupled to a controller and a liquid delivery device, typically a pump or other motive force for fluid delivery, in a closed loop, so that the difference between the sensed system parameter value and the set point controls actuation of the pump.

Basically, any sensor that can detect specific parameters of the system fluids and flows and output a measurable (analog or digital) signal may be used, such as sensors based on spectral measurement (e.g. near IR, UV) or ionic measurement (conductivity, pH).

The in-line adjustment means is typically operated by a computerized control which may be separate form or the same as the computerized control and data analysis system used to operate the STP system. With respect to the above-mentioned case of protein purification, for example, the in-line adjustment will perform closed loop control of pH, conductivity and UV, while stepped, steep sloped and shallow sloped changes of these parameters occur in the process feed stream.

Figure 2:
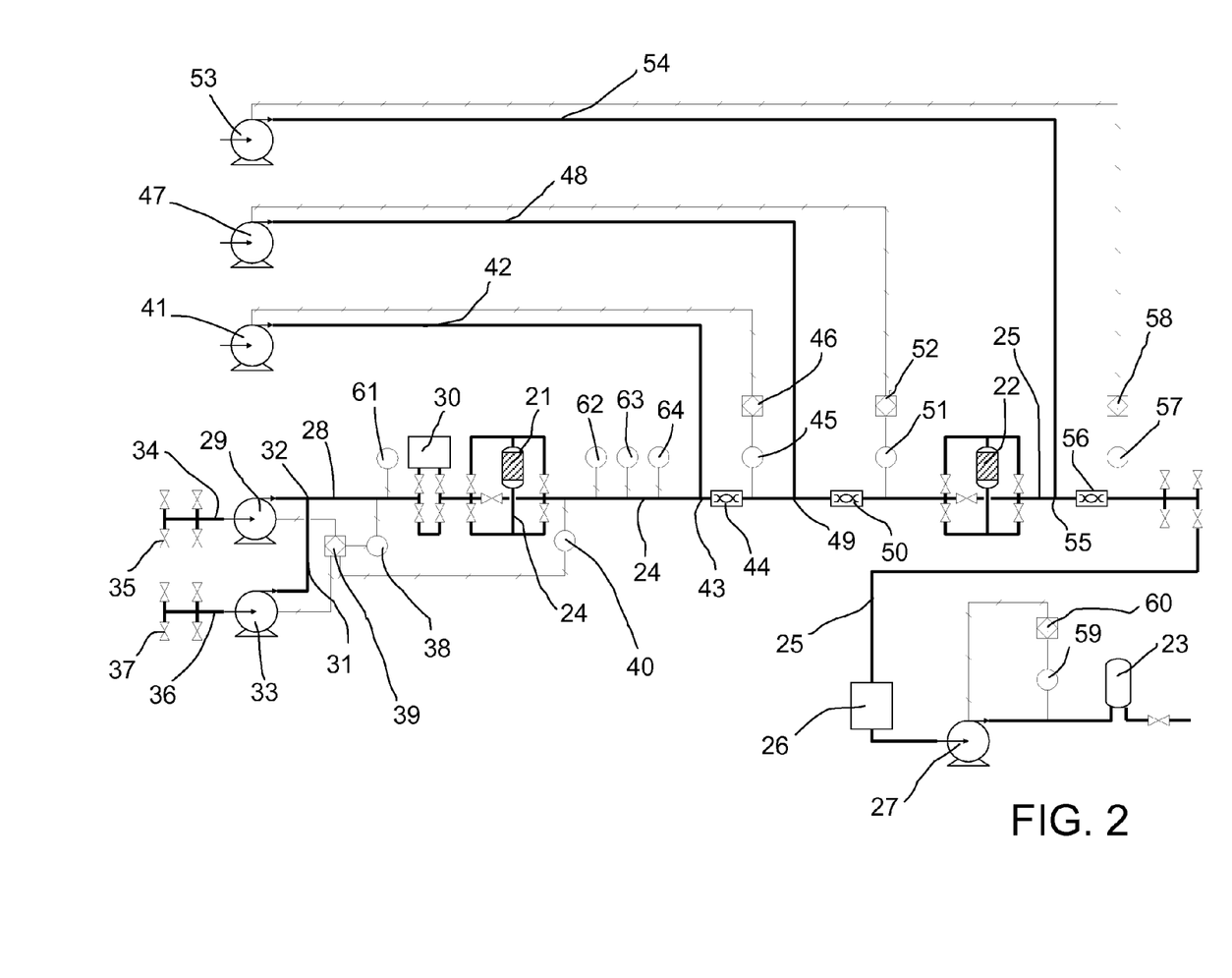
FIG. 2 is a diagram of a chromatography system configuration according to an embodiment of the present invention.

FIG. 2 shows the configuration of an embodiment of chromatography system according to the invention designed for downstream purification of proteins, particularly monoclonal antibodies.

The chromatography system includes three separation units, i.e. a cation exchange column 21, an anion exchange column 22 and a virus removal filter 23 connected in series. Specifically, column 21 is coupled to column 22 through a conduit 24, and column 22 is coupled to the virus removal filter 23 through a conduit 25 via valves, a pressure break tank 26 and a pump 27.

The inlet of chromatography column 21 is connected through a conduit 28 to a first chromatography pump 29 via valves and a bubble trap 30, and through a conduit 31 connecting to conduit 28 at a T-junction 32, to a second chromatography pump 33. The first pump 29 has an inlet line 34 with (here) four inlet valves 35, one of which serves as sample valve. Likewise, the second pump 33 has an inlet line 36 with (here) four inlet and sample valves 37.

A closed loop control circuit (PID) controls the operation of chromatography pumps 29 and 33 and includes an in-line conductivity sensor 38 for sensing the conductivity of inlet conduit 28 and connected to a controller 39, which is in turn connected to pumps 29 and 33. To the controller 39 is also connected in a closed loop fashion an in-line flow sensor 40 coupled to conduit 24 connecting chromatography columns 21 and 22.

The chromatography pumps 29 and 33 correspond to gradient pumps conventionally used in chromatography, and the closed loop control circuit described above corresponds to standard conductivity feedback adjustment logic provided on gradient systems.

The illustrated chromatography system includes four in-line adjustment arrangements.

A first in-line adjustment arrangement is for adjusting the conductivity of the outflow from chromatography column 21, and comprises a buffer pump 41 which is connected to conduit 24 via a conduit 42 at a T-junction 43 adjacent to a downstream mixer 44. A PID closed loop control circuit is provided to control the operation of pump 41, including an in-line conductivity sensor 45 coupled to conduit 24 downstream of the mixer 44. The conductivity sensor 45 is connected to a controller 46 which in turn is connected to pump 41. The PID loop reads the conductivity from sensor 45 and adjusts the pump 41 to reach and maintain the desired set point.

A second in-line adjustment arrangement adjusts the pH of the outflow from chromatography column 21 and comprises a buffer pump 47 which is connected to conduit 24 via a conduit 48 at a T-junction 49 adjacent to a downstream mixer 50. A PID closed loop control circuit is provided to control the operation of pump 47, including an in-line pH sensor 51 coupled to conduit 24 downstream of the mixer 50. The pH sensor 51 is connected to a controller 52 which in turn is connected to pump 47. The PID loop reads the pH from sensor 51 and adjusts the pump 47 to reach and maintain the desired set point.

A third in-line adjustment arrangement adjusts the UV absorbance (product concentration) of the outflow from the second chromatography column 22 in conduit 25 and comprises a buffer pump 53 which is connected to conduit 25 via a conduit 54 at a T-junction 55 adjacent to a downstream mixer 56. A PID closed loop control circuit controls the operation of pump 53, including an in-line UV sensor 57 coupled to conduit 25 downstream of the mixer 56. The UV sensor 57 is connected to a controller 58 which in turn is connected to pump 53. The PID loop reads the UV absorbance from sensor 57 and adjusts the pump 53 to reach and maintain the desired set point.

A fourth in-line adjustment arrangement is provided for final adjustment of the UV absorbance (product concentration) of the product flow in conduit 25 downstream of the pressure break tank 26. This in-line adjustment arrangement comprises dilution buffer pump 27 and a PID closed loop control circuit which controls the operation of pump 27, including an in-line UV sensor 59 coupled to conduit 25 between the pump 27 and the virus removal filter 23, and a controller 60. The PID loop reads the UV absorbance from sensor 59 and adjusts the pump 27 to reach and maintain the desired set point, which is selected to correspond to a dilution before filtration only to an extent necessary to avoid clogging of the filter.

In-line adjustment of the conductivity and/or pH of the product flow during load on the first column may be provided by the chromatography pumps 29 and 33 together with the associated PID control circuit 38, 39, and may, optionally, be considered as a fifth in-line adjustment arrangement.

The illustrated chromatography system further comprises an in-line pressure sensor 61 upstream of the bubble trap 30, and in-line conductivity, pH and UV sensors 62, 63 and 64, respectively, downstream of the column 21 but upstream of junction 43. The virus removal filter 23 may, for example, be a membrane filter.

The different pumps in the chromatography system may, for example, be selected from peristaltic pumps, piston pumps and diaphragm pumps.

The mixers 44, 50, 56 may be static mixers, such as in-tube or a size segment of piping that increases and then decreases the inside diameter, resulting in a turbulent flow in the stream.

The chromatography system is controlled by control software. Exemplary such control software includes the UNICORN™ control system (GE Healthcare Bio-Sciences AB, Uppsala, Sweden), which is based on a controller and I/O interface with a computer graphical user interface, being an integral part of the control system.

The system shown in FIG. 2 and described above could perform in various ways. In the following, three exemplary uses will be described for illustration:

1. First column (21) in bind-elute mode and final viral filtration (23)
2. First column (21) in bind-elute mode, second column (22) in capture mode (flow-through), and final viral filtration (23)
3. First column (21) in bind-elute mode, second column (22) in bind-elute mode, and final viral filtration (23)

1. First Column in Bind-Elute Mode and Final Viral Filtration

The first column 21 is equilibrated, either with a previously prepared solution, or with buffer prepared in real time using an in-line buffer preparation unit or arrangement, such as that disclosed in the above-mentioned co-pending application "Method and system for preparation of liquid mixtures". The sample is then loaded onto the column 21, either directly, or with an adjustment of conductivity or pH via pump 33 and control circuit 38, 39, 40. After the sample is bound and a wash of the unbound sample is complete, the protein is eluted.

Elution can be isocratic with fixed pH or conductivity, supplied either with a previously prepared solution, or with buffer prepared using an in-line buffer preparation unit if the separation system is so equipped. Alternatively, a gradient elution of flow or conductivity can be applied with the pumps 29, 33 and control circuit 39, 38, 40. Gradient elution allows the target set point for the mix between the pumps to vary at a linear rate, and a control algorithm of the system control causes the mix to follow this changing linear set point.

Optionally, while eluting out of the column 21, the conductivity can be adjusted in-line to specified values during elution via the first in-line adjustment arrangement including pump 41, conduit 42, T-junction 43, mixer 44 and the conductivity control circuit 45, 46. Likewise, pH can be adjusted in-line via the second in-line adjustment arrangement including pump 47, conduit 48, T-junction 49, mixer 50 and the pH control circuit 51, 52; and the protein concentration can be adjusted in-line via the third in-line adjustment arrangement comprising pump 53, conduit 54, T-junction 55, mixer 56 and the UV control circuit 57, 58.

The concentration adjusted product continues through the filter 23 at constant pressure using pump 27 and the UV control circuit 59, 60.

2. First Column in Bind-Elute Mode, Second column in Capture Mode (Flow-Through), and Final Viral Filtration The first 21 and second 22 columns are equilibrated, either with a previously prepared solution, or with buffer prepared in real time using the in-line buffer preparation capabilities of the system if so equipped. If the equilibration solutions are the same for the two columns, this can be performed in-line with one another; otherwise, the equilibrations would be performed sequentially, with the other column by-passed.

The sample is then loaded onto the column 21, either directly, or with an adjustment of conductivity 33, 38 or pH 39, 40. During this operation, the second column 22 may be in-line or by-passed, depending on the process requirements. After the sample is bound and a wash of the unbound sample is complete, the protein is eluted.

During the elution, the second column 22 is put in-line, if not already in-line. Elution can be isocratic with fixed pH or conductivity, supplied either from a previously prepared solution, or with buffer prepared using in-line buffer preparation capabilities of the system if so equipped. Alternatively, a gradient elution of flow or conductivity can be applied with the pumps 29, 33 and control circuit 39, 38, 40. Gradient elution allows the target set-point for the mix between the pumps to vary at a linear rate, and a control algorithm of the system control causes the mix to follow this changing linear set-point.

Optionally, while eluting out of the first column 21, the conductivity and/or pH can be adjusted in-line to meet the application requirements of the second column 22, conductivity being adjusted via the first in-line adjustment arrangement including pump 41, conduit 42, T-junction 43, mixer 44 and control circuit 45, 46, and pH via the second in-line adjustment arrangement including pump 47, conduit 48, T-junction 49, mixer 50 and control circuit 51, 52.

Out of the second column 22 the protein concentration can be adjusted in-line to specified values through the third in-line adjustment arrangement including pump 53, conduit 54, T-junction 55, mixer 56 and control circuit 57, 58.

The concentration adjusted product continues through the filter 23 at constant pressure using pump 27 and control circuit 59, 60.

It is to be noted that the system could also be easily configured before the run (or during the run with additional valves added) to change the location of the intermediate conductivity adjustment loop 41, 42, 43, 44, 45, 46 (the first in-line adjustment arrangement) and pH adjustment loop 47, 48, 49, 50, 51, 52 (the second in-line adjustment arrangement) to allow adjustment after the second column 22 if needed to meet process requirements.

3. First Column in Bind-Elute Mode, Second Column in Bind-Elute Mode, and Final Viral Filtration The first 21 and second 22 columns are equilibrated, either with a previously prepared solution, or with buffer prepared in real time using the in-line buffer preparation capabilities of the system if so equipped. If the equilibration solutions are the same for the two columns, this can be performed in-line with one another; otherwise, the equilibrations would be performed sequentially, with the other column by-passed. The filter 23 is not in-line at this time.

The sample is loaded onto the column 21, either directly, or with an adjustment of conductivity or pH through pump 33 and control circuit 38, 39, 40. During this operation, the second column 22 is by-passed. After the sample is bound and a wash of the unbound sample is complete, the protein is eluted.

Elution can be isocratic with fixed pH or conductivity, supplied either from a previously prepared solution, or with buffer prepared using the in-line buffer preparation capabilities of the system if so equipped. Alternatively, a gradient elution of flow or conductivity can be applied with the pumps 29, 33 and control circuit 39, 38, 40. Gradient elution allows the target set-point for the mix between the pumps to vary at a linear rate, and a control algorithm of the system control causes the mix to follow this changing linear set-point.

During the elution from the first column 21, the second column 22 is in-line, and the eluate from the first column 21 binds to the second column 22. Optionally, while eluting out of the first column 21 the conductivity and/or pH can be adjusted in-line to meet the application requirements for binding to the second column 22, conductivity being adjusted through the first in-line adjustment arrangement including pump 41, conduit 42, T-junction 43, mixer 44 and control circuit 45, 46, and pH being adjusted through the second in-line adjustment arrangement including pump 47, conduit 48, T-junction 49, mixer 50, and control circuit 51, 52.

After all protein from the first column 21 is bound to the second column 22, the first column 21 is by-passed, and the second column 22 is washed of unbound sample. When the wash of the second column 22 is complete, the filter 23 is put in-line, and elution from the second column 22 begins.

Elution can be isocratic with fixed pH or conductivity, supplied either from a previously prepared solution, or with buffer prepared using the in-line buffer preparation capabilities of the system if so equipped. Alternatively, a gradient elution of flow or conductivity can be applied with the pumps 29, 33 and control circuit 39, 38, 40. Gradient elution allows the target set-point for the mix between the pumps to vary at a linear rate, and a control algorithm of the system control causes the mix to follow this changing linear set-point.

Out of the second column 22 the protein concentration can be adjusted inline to specified values using the third in-line adjustment arrangement including pump 53, conduit 54, T-junction 55, mixer 56 and control circuit 57, 58. The eluting product is continuously pumped through the filter 23 by pump 27 at constant pressure via control circuit 59, 60.

It is to be noted that the system could also be easily configured before the run (or during the run with additional valves added) to change the location of the intermediate conductivity adjustment loop 41, 42, 43, 44, 45, 46 (the first in-line adjustment arrangement) and pH adjustment loop 47, 48, 49, 50, 51, 52 (the second in-line adjustment arrangement) to allow adjustment after the second column 22 if needed to meet process needs.

In the following, experiments performed with test platforms demonstrating the functionality of the invention will be described.

EXAMPLES

Below the present invention will be disclosed by way of examples, which are intended solely for illustrative purposes and should not be construed as limiting the present invention as defined in the appended claims. All references mentioned below or elsewhere in the present application are hereby included by reference.

The functionality of the above described embodiment of an STP system of the invention, which includes two columns and virus filtration in series, was demonstrated by tests performed with two model monoclonal antibody (Mab) products on two test platforms, each including a single column and no virus filter.

The two test platforms were based on a standard 10 mm BioProcess polypropylene system (GE Healthcare Bio-Sciences AB, Uppsala, Sweden) with a number of additional features engineered into the system.

Test Platform I

Figure 3:
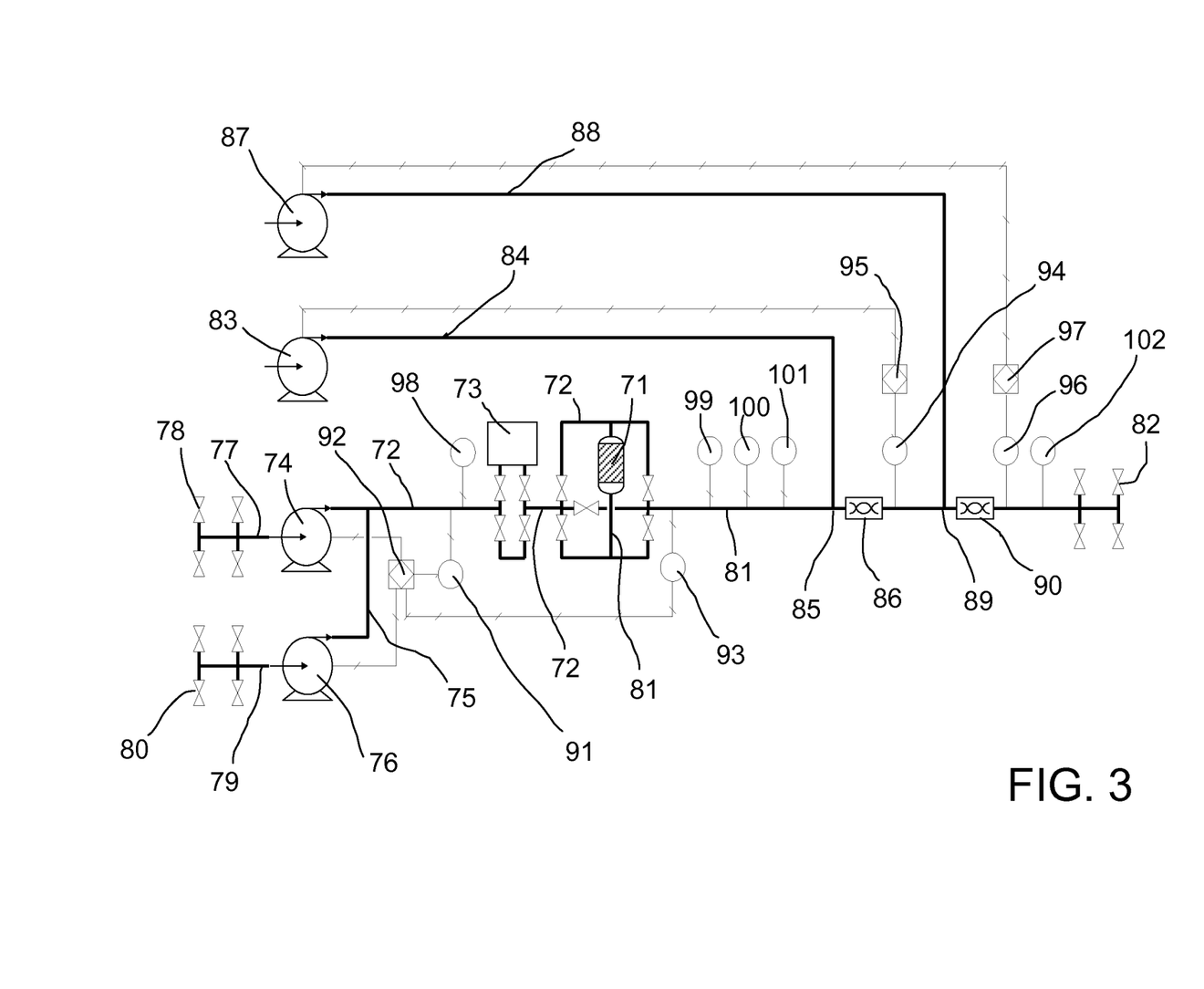
FIG. 3 is a diagram of chromatography system test platform configuration used for testing features of the chromatography system of FIG. 2.

FIG. 3 shows the chromatography system configuration for the first test platform, used for a first model monoclonal antibody DPC (direct product capture) product, below referred to as "Mab 1".

The inlet of a chromatography column 71 is connected via a conduit 72 containing a bubble trap 73 to a first diaphragm chromatography pump 74 (Lewa GmbH, Leonberg, Germany), and via a conduit 75 connecting to conduit 72 to a second diaphragm chromatography pump 76 (Lewa GmbH). The pump 74 has an inlet conduit 77 with (here) four inlet valves 78, one of which serves as sample valve. Likewise, the pump 76 has an inlet conduit 79 with (here) four inlet and sample valves 80. The outlet of the column 71 connects via a conduit 81 to (here) four outlet valves 82, one of which is for waste.

A first peristaltic titration buffer pump 83 (Watson-Marlow 604IU IP55; Watson-Marlow Inc., Wilmington, Mass., USA) is connected to the column outlet conduit 81 via a conduit 84 at a T-junction 85. An in-pipe static mixer 86 is provided downstream of junction 85. A second peristaltic titration buffer pump 87 (Watson-Marlow 520DU IP31) connects to outlet conduit 81 via a conduit 88 at a T-junction 89, and an in-pipe static mixer 90 is provided downstream of junction 89.

A first PID closed loop control circuit controls the operation of chromatography pumps 74 and 76 and includes an in-line conductivity sensor 91 (CMC-DNB, CM-P; GE Healthcare Bio-Sciences AB) for sensing the conductivity of inlet conduit 72 and connected to a controller 92 (UNICORN™; GE Healthcare Bio-Sciences AB), which is in turn connected to pumps 74 and 76. To the controller 92 is also connected in a closed loop fashion an in-line flow sensor 93

(PROMASS™ M, 60 MT-AUG00A00B2B; Endress+ Hauser, Reinach, Switzerland) coupled to the column outlet conduit 81.

A second PID closed loop control circuit controls the operation of titration buffer pump 83 and includes an in-line UV sensor 94 (for sensing product concentration) (Optical Unit UV1, UV-P; GE Healthcare Bio-Sciences AB) coupled to column outlet conduit 81 between mixer 86 and T-junction 89. UV sensor 94 is connected to a controller 95 (UNICORN™; GE Healthcare Bio-Sciences AB) which in turn is connected to pump 83.

A third PID closed loop control circuit controls the operation of titration buffer pump 87 and includes an in-line pH sensor 96 (pH Sensor, Endress+Hauser; Transmitter pH-P; GE Healthcare Bio-Sciences AB) coupled to column outlet conduit 81 downstream of mixer 90. pH sensor 96 is connected to a controller 97 (UNICORN™; GE Healthcare Bio-Sciences AB) which in turn is connected to pump 87.

The illustrated chromatography test platform further comprises an in-line pressure sensor 98 upstream of the column 71, in-line conductivity, pH and UV sensors 99, 100 and 101, respectively, downstream of the column 71 but upstream of mixer 86, and an in-line conductivity sensor 102 downstream of pH sensor 96.

Buffer-Only Runs

Prior to performing any runs on the actual proteins, a series of buffer-only runs were performed to verify operation of the control loops integrated into the system, and profile the capability of the control for conductivity, pH and UV (protein concentration) in transition and stationary states. The respective control circuits were used to control a process stream at a set value.

Mab 1 Product Experiments

Experiments were then run with the Mab 1 monoclonal antibody product, the goals being (i) to demonstrate in-line dilution of sample during load to a target conductivity, (ii) to demonstrate post-column adjustment of pH during elution, and (iii) to demonstrate post-column adjustment of protein concentration (UV) during elution.

The column 71 was a 25 cm chromatography column (BPG™, GE Healthcare Bio-Sciences AB, Uppsala, Sweden) packed with SP SEPHAROSE™ XL cation chromatographic resin (GE Healthcare Bio-Sciences AB). The flow rate was 200 cm/h for all steps except elution which was performed at 150 cm/h.

The following buffers were used for the cation exchange chromatography process:
Sanitization: 1.0 mM NaOH
Equilibration/wash to baseline: 30 mM sodium phosphate, pH 6.5
Elution buffer: 30 mM sodium phosphate, 50 mM NaCl, pH 6.5
Strip buffer: 50 mM Tris, 1.0 M NaCl, pH 8.0
Storage buffer: 0.1 M NaOH Conductivity adjustment pre-column for sample load was performed by the feedback control loop including conductivity sensor 91 and controller 92.

Post-column, the UV was adjusted using elution buffer as the diluent fed by peristaltic pump 83 into T-junction 85 and was then mixed through mixer 86 (a size change segment of piping that increases, then decreases the inside diameter). The PID loop coupled to pump 83 including sensor 94 and controller 95 read the UV from sensor 94 downstream of the mixer 86 and adjusted the pump 83 to reach the set point.

pH adjustment was made after the UV adjustment and used Tris buffer as the adjustment buffer, fed by peristaltic pump 87 into outlet conduit 81 through a T-junction 89 downstream of mixer 86 and to an in-pipe static mixer 90 in the stream producing a turbulent flow. The PID loop coupled to pump 87 read the pH from sensor 96 downstream of the mixer 90 and adjusted the pump 87 to reach the set point.

Test Platform II

Figure 4:
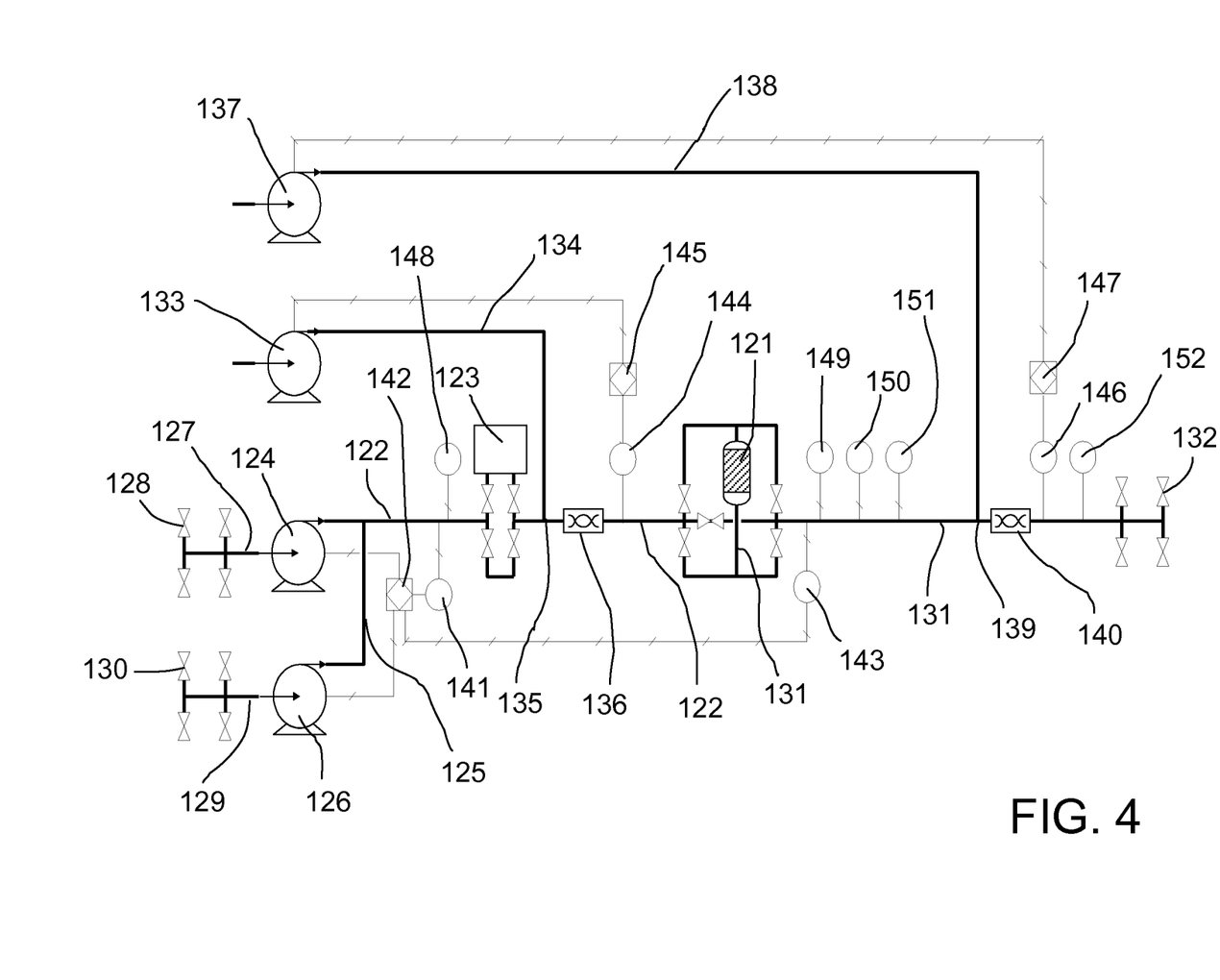
FIG. 4 is a diagram of another chromatography system test platform configuration used for testing features of the chromatography system of FIG. 2.

FIG. 4 shows the chromatography system configuration for the second test platform, used for a second model monoclonal antibody DPC (direct product capture) product, below referred to as "Mab 2".

The inlet of a chromatography column 121 is connected via a conduit 122 containing a bubble trap 123 to a first diaphragm chromatography pump 124 (Lewa GmbH, Leonberg, Germany), and via a conduit 125 connecting to conduit 122 to a second diaphragm chromatography pump 126 (Lewa GmbH). The pump 124 has an inlet conduit 127 with (here) four inlet valves 128, one of which serves as sample valve. Likewise, the pump 126 has an inlet conduit 129 with (here) four inlet and sample valves 130. The outlet of the column 121 connects via a conduit 131 to (here) four outlet valves 132, one of which is for waste.

A first piston titration buffer pump 133 (Pump P900; GE Healthcare Bio-Sciences AB, Uppsala, Sweden) is connected to the column inlet conduit 122 via a conduit 134 at a T-junction 135 downstream of bubble trap 123. An in-pipe static mixer 136 is provided downstream of junction 135. A second peristaltic titration buffer pump 137 (Watson-Marlow 604U IP55) connects to column outlet conduit 131 via a conduit 138 at a T-junction 139, and an in-pipe static mixer 140 is provided downstream of junction 139.

A first PID closed loop control circuit controls the operation of chromatography pumps 124 and 126 and includes an in-line conductivity sensor 141 (CMC-DN8, CM-P; GE Healthcare Bio-Sciences AB) for sensing the conductivity of inlet conduit 122 and connected to a controller 142, which is in turn connected to pumps 124 and 126. To the controller 142 is also connected in a closed loop fashion an in-line flow sensor 143 coupled to the column outlet conduit 131.

A second PID closed loop control circuit controls the operation of titration buffer pump 133 and includes an in-line pH sensor 144 (pH Sensor, Endress+Hauser; Transmitter pH-P; GE Healthcare Bio-Sciences AB) coupled to column inlet conduit 122 between mixer 136 and column 121. pH sensor 144 is connected to a controller 145 which in turn is connected to pump 133.

A third PID closed loop control circuit controls the operation of titration buffer pump 137 and includes an in-line UV sensor 146 (Optical Unit UV1, UV-P; GE Healthcare Bio-Sciences AB) coupled to column outlet conduit 131 downstream of mixer 140. UV sensor 146 is connected to a controller 147 which in turn is connected to pump 137.

The illustrated chromatography test platform further comprises an in-line pressure sensor 148 upstream of the bubble trap 123, in-line conductivity, pH and UV sensors 149, 150 and 151, respectively, between column 121 and T-junction 139, and an in-line conductivity sensor 152 downstream of UV sensor 146.

Mab 2 Product Experiments

Experiments were then run with the Mab 2 monoclonal antibody product, the goals being (i) to demonstrate in-line pre-column adjustment of pH (down) during sample load, and (ii) to demonstrate post-column adjustment of protein concentration (UV) during elution.

The column 121 was a 25 cm chromatography column (BPG™; GE Healthcare Bio-Sciences AB, Uppsala, Sweden) packed with SP SEPHAROSE™ XL cation chromatographic resin (GE Healthcare Bio-Sciences AB). The flow rate was 250 cm/h for all steps.

The following buffers were used for the cation exchange chromatography process:
MMC load pH adjustment: 2.0 M acetate
Sanitization: 1.0 mM NaOH
Equilibration/wash to baseline: 100 mM acetate, pH 5.0
Intermediate wash: 25 mM citrate, 200 mM NaCl, pH 5.0
Elution buffer: 25 mM citrate, 225 mM NaCl, pH 5.6
Strip buffer: 25 mM citrate, 1.0 M NaCl, pH 5.4
Storage buffer: 0.1 M NaOH Pre-column-pH adjustment was made using 2M acetic acid as the adjustment buffer, fed by a P900 positive displacement pump (GE Healthcare Bio-Sciences AB, Uppsala, Sweden), into T-junction 135 with static mixer 136 in the stream, producing a turbulent flow. The PID loop including controller 145 read the pH from sensor 144 downstream of the pH static mixer 136 and adjusted the pump 133 to reach the set point.

Post-column, the UV was adjusted using elution buffer as the diluent, fed by a peristaltic pump into the stream at piping T-segment junction 139 and mixer 140, to provide the mixing mechanism. The PID loop including controller 147 read the UV from sensor 146 downstream of the T-union 139 and adjusted the pump 137 to reach the set point.

RESULTS/CONCLUSIONS

The buffer runs showed that the system is capable of responding to a number of dynamic conditions, provided the pumps are operating in their linear operating range.

The Mab 2 sample runs demonstrated that the system could respond to samples with different starting conductivities, and successfully load and bind to the column. Sample load with in-line dilution demonstrated the automatic adjustment of the load parameters assuring the proper load conditions are met, regardless of differences in the starting conductivity or pH of the sample batches. The technology is thus able to adjust the conditions to assure the load is successful without manual operations to adjust the batch. Based on UV measurements during load, no product was lost.

Successful post-column pH adjustment was also demonstrated as well as the post-column protein concentration control. pH adjustment showed the ability to adjust the pH eluting off a column, that might prepare it for loading onto a second column or other separation device. Performing the adjustment in-line allows the system to react to the changing conditions of the elution stream, assuring the antibody or protein is properly prepared for the next column or spends the minimum time in the unstable conditions. This is not possible to achieve in a tank batch adjustment mode. Thus, the STP system eliminates the need for a vessel between columns 1 and 2 in an antibody purification system of the type in question.

Sample concentration adjustment was effective in assuring that the concentration stayed below a level that might result in premature virus filter clogging downstream of the second column in an antibody purification system. Once again, adjustment in-line allows the system to react, saving time and labour of diluting post-run, enabling the straight through application of the stream onto a sterile filtration step, and improving the quality by removing manual interaction. Thus the STP system eliminates the need for a vessel to make the adjustments between column 2 and the virus filter in an antibody purification system.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A separation system for the separation and purification of biomolecules, said separation system comprising:
    first and second chromatography devices connected in series, the first chromatography device comprising a fluid outlet and the second chromatography device comprising a fluid inlet, wherein the fluid outlet and inlet are connected by a main conduit, wherein the first chromatography device provides an outflow liquid to the main conduit;
    a fluid-delivery device operably coupled to a controller and fluidly coupled to the main conduit through a branch conduit that joins the main conduit at a junction between the first and second chromatography devices, the fluid-delivery device configured to provide a continuous stream of an incoming liquid into the main conduit to be mixed with the outflow liquid to form a mixed liquid; and
    an in-line sensor operably coupled to (i) the main conduit between the junction and the inlet of the second chromatography device and (ii) the controller, the in-line sensor configured to measure an in-time environmental property parameter of the mixed liquid to provide it to the controller,
    wherein a flow rate of the incoming liquid provided by the fluid-delivery device is controlled by the controller based on the in-time measurements of the environmental property parameter of the mixed liquid; and
    a virus removal filter positioned downstream from and coupled to the second chromatography device.

2. The separation system of claim 1 further comprising a third chromatography device having a fluid inlet, the second chromatography device having a fluid outlet that is connected to the fluid inlet of the third chromatography device wherein the in-line sensor and the fluid-delivery device constitute a first adjustment assembly, the separation system further comprising a second adjustment assembly having an in-line sensor and a fluid-delivery device that are operably coupled to a main conduit that joins the second and third chromatography devices.

3. The separation system of claim 1, wherein the fluid delivery device comprises at least one pump.

4. The separation system of claim 1, wherein the environmental property parameter is at least one of pH, conductivity, or species concentration.

5. The separation system of claim 4, wherein the in-line sensor comprises a UV sensor.

6. The separation system of claim 1, wherein the chromatography devices comprise a cation exchange column and an anion exchange column.

7. The separation system of claim 6, wherein the in-line sensor and the fluid-deliver device are configured to monitor and adjust at least one of conductivity or pH of the mixed liquid.

8. The separation system of claim 6, wherein the in-line sensor and the fluid-delivery device are configured to monitor and adjust UV absorbance of the mixed liquid.

9. The separation system of claim 1, wherein the main conduit directly couples the first and second chromatography devices such that all of the outflow liquid provided by the first chromatography device flows to the second chromatography device through the main conduit.

10. The separation system of claim 1, wherein the main conduit directly couples the first and second chromatography devices such that the outflow liquid from the first chromatography device in the main conduit does not flow into an intermediate holding tank before the fluid inlet.

11. The separation system of claim 1, wherein the controller comprises a computing system that automatically controls the flow rate of the incoming liquid, the flow rate being based on a difference between the measurement of the environmental property parameter and a designated value.

12. The separation system of claim 1, further comprising a mixer located downstream from the junction and upstream from the in-line sensor that mixes the incoming and outflow liquids to form the mixed liquid.

13. The separation system of claim 1, wherein the main conduit includes a segment that has a varying diameter that is downstream from the junction, the varying diameter causing a turbulent flow.

14. The separation system of claim 1, wherein the controller comprises a computing system that automatically controls the flow rate of the incoming liquid, the flow rate being based on a difference between the measurement of the environmental property parameter and a designated value of the environmental property parameter, wherein the environmental property parameter is conductivity.

15. The separation system of claim 1, wherein the in-line sensor, the controller, and the fluid-delivery device constitute a first adjustment assembly and the separation system further comprises a second adjustment assembly comprising:
a second fluid-delivery device operably coupled to a second controller and fluidly coupled to the main conduit through a second branch conduit that joins the main conduit at a second junction downstream from the junction of the first adjustment assembly and before the second chromatography device, wherein the second fluid-delivery device is configured to provide a continuous stream of a second incoming liquid into the main conduit to be mixed with the mixed liquid from the first assembly to form a second mixed liquid; and
a second in-line sensor operably coupled to (i) the main conduit between the second junction and the inlet of the second chromatography device and (ii) the second controller, the second in-line sensor configured to measure an in-time environmental property parameter of the second mixed liquid to provide it to the second controller;
wherein a flow rate of the second incoming liquid provided by the second fluid-delivery device is controlled by the second controller based on the in-time measurements of the environmental property parameter of the second mixed liquid.

16. The separation system of claim 1, wherein the in-lien sensor, the controller, and the fluid-delivery device constitute a first adjustment assembly and the second chromatography device comprises a fluid outlet operably connected to a second main conduit and the second chromatography device provides an outflow liquid to the second main conduit;
wherein the separation system further comprises another adjustment assembly comprising:
another fluid-delivery device operably coupled to another controller and fluidly coupled to the second main conduit through another branch conduit that joins the second main conduit at another junction, wherein said another fluid-delivery device is configured to provide a continuous stream of another incoming liquid into the second main conduit to be mixed with the outflow liquid from the second chromatography device to form another mixed liquid; and
another in-line sensor operably coupled to (i) the second main conduit between said another junction and the filter and (ii) said another controller, said another in-line sensor configured to measure an in-time environmental property parameter of said another mixed liquid to provide it to said another controller;
wherein a flow rate of said another incoming liquid provided by said another fluid-delivery device is controlled by said another controller based on the in-time measurement of the environmental property parameter of said another mixed liquid.

17. The separation system of claim 1, wherein the in-line sensor, the controller, and the fluid-delivery device constitute a first adjustment assembly and the separation system further comprises an inlet adjustment assembly comprising:
one or more inlet fluid-delivery device(s) operably coupled to an inlet controller and fluidly coupled to an inlet conduit through an inlet branch conduit that joins the inlet conduit at an inlet junction upstream of the inlet of the first chromatography device, wherein the inlet fluid-delivery device(s) are configured to provide a continuous stream of an inlet incoming liquid into the inlet conduit; and
one or more inlet in-line sensor(s) operably coupled to (i) the inlet and/or main conduit(s) and (ii) the inlet controller, the inlet in-line sensor(s) configured to measure an in-time environmental property parameter(s) of the inlet incoming liquid and/or the outflow liquid to provide them to the inlet controller;
Wherein the flow rate of the inlet incoming liquid provided by the inlet fluid-delivery device(s) is controlled by the inlet controller based on the in-time measurements of the environmental property parameter(s) of the inlet incoming liquid and/or the outflow liquid.

18. A separation system for the separation and purification of biomolecules, said separation system comprising:
first and second chromatography devices connected in series, the first chromatography device comprising a fluid outlet and the second chromatography device comprising a fluid inlet, wherein the fluid outlet and inlet are connected by a main conduit, wherein the first chromatography device provides an outflow liquid to the main conduit;
a fluid-delivery device operably coupled to a controller and fluidly coupled to the main conduit through a branch conduit that joins the main conduit at a junction between the first and second chromatography devices, the fluid-delivery device configured to provide a continuous stream of an incoming liquid into the main conduit to be mixed with the outflow liquid to form a mixed liquid; and
an in-line sensor operably coupled to (i) the main conduit between the junction and the inlet of the second chromatography device and (ii) the controller, the in-line sensor configured to measure an in-time environmental property parameter of the mixed liquid to provide it to the controller;
wherein a flow rate of the incoming liquid provided by the fluid-delivery device is controlled by the controller based on the in-time measurements of the environmental property parameter of the mixed liquid; and
a virus removal filter positioned downstream from and coupled to the second chromatography device, and
wherein the in-line sensor, the controller, and the fluid-delivery device constitute a first adjustment assembly and the separation system further comprises a second adjustment assembly comprising:

a second fluid-delivery device operably coupled to a second controller and fluidly coupled to the main conduit through a second branch conduit that joins the main conduit at a second junction downstream from the junction of the first adjustment assembly and before the second chromatography device, wherein the second fluid-delivery device is configured to provide a continuous stream of a second incoming liquid into the main conduit to be mixed with the mixed liquid from the first assembly to form a second mixed liquid; and a second in-line sensor operably coupled to (i) the main conduit between the second junction and the inlet of the second chromatography device and (ii) the second controller, the second in-line sensor configured to measure an in-time environmental property parameter of the second mixed liquid to provide it to the second controller;

wherein a flow rate of the second incoming liquid provided by the second fluid-delivery device is controlled by the second controller based on the in-time measurements of the environmental property parameter of the second mixed liquid, and wherein the second chromatography device comprises a fluid outlet operably connected to a second main conduit and the second chromatography device provides an outflow liquid to the second main conduit;

wherein the separation system further comprises a third adjustment assembly comprising:

a third fluid-delivery device operably coupled to a third controller and fluidly coupled to the second main conduit through a third branch conduit that joins the second main conduit at a third junction, wherein the third fluid-delivery device is configured to provide a continuous stream of a third incoming liquid into the second main conduit to be mixed with the outflow liquid from the second chromatography device to form a third mixed liquid; and a third in-line sensor operably coupled to (i) the second main conduit between the third junction and the filter and (ii) the third controller, the third in-line sensor configured to measure an in-time environmental property parameter of the third mixed liquid to provide it to the third controller;

wherein a flow rate of the third incoming liquid provided by the third fluid-delivery device is controlled by the third controller based on the in-time measurements of the environmental property parameter of the third mixed liquid.

19. The separation system of claim 18, wherein the fluid delivery device in the assemblies comprises at least one pump, the environmental property parameter is at least one of pH, conductivity, or species concentration, the chromatography devices comprise a cation exchange column and an anion exchange column, and the in-line sensor and the fluid-delivery device in the assemblies are configured to monitor and adjust at least one of conductivity, pH, or UV of the respective mixed liquids.

20. The separation system of claim 18, wherein the controllers of the assemblies comprise a computing system that automatically controls the flow rate of the incoming liquids, the flow rate being based on a difference between measurements of the respective environmental property parameter and a designated value of the respective environmental property parameter.

* * * * *